(12) United States Patent
Clark et al.

(10) Patent No.: US 7,402,432 B2
(45) Date of Patent: Jul. 22, 2008

(54) PROCESS FOR PRODUCING T LYMPHOCYTES

(75) Inventors: Rachael A. Clark, Belmont, MA (US); Thomas Kupper, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 363 days.

(21) Appl. No.: 11/005,481

(22) Filed: Dec. 7, 2004

(65) Prior Publication Data

US 2005/0208654 A1 Sep. 22, 2005

Related U.S. Application Data

(60) Provisional application No. 60/528,796, filed on Dec. 12, 2003.

(51) Int. Cl.
*C12N 5/06* (2006.01)
(52) U.S. Cl. ............... 435/373; 435/377; 435/395; 435/372.3; 435/372
(58) Field of Classification Search ................ None
See application file for complete search history.

(56) References Cited

U.S. PATENT DOCUMENTS

| 6,548,299 | B1 | 4/2003 | Pykett et al. |
| 7,192,769 | B2 | 3/2007 | Pykett et al. |
| 2001/0014320 | A1 | 8/2001 | Waller |
| 2002/0064874 | A1 | 5/2002 | Vie et al. |

OTHER PUBLICATIONS

International Search Report Dated Jul. 17, 2006.
Edmund K. Waller et al., "Irradiated Donor Leukocytes Promote Engraftment of Allogeneic Bone Marrow in Major Histocompatibility Complex Mismatched Recipients Without Causing Graft-Versus-Host Disease", Blood, vol. 94, No. 9, Nov. 1, 1999: pp. 3222-3233.
Rachael A. Clark et al., "Human Skin Cells Support Thymus-Independent T Cell Development", The Journal of Clinical Investigation, vol. 115, No. 11, Nov. 15, 2005.
Anderson, et al., "Lymphostromal Interactions in Thymic Development and Function," *Nat. Rev. Immunol.* 1:31-40 (2001).
Freedman, et al., "Generation of Human T Lymphocytes from Bone Marrow CD34+ Cells in vitro," *Nature Medicine* 2:46-51 (1996).
Galy, et al., "Human T, B, Natural Killer, and Dendritic Cells Arise from a Common Bone Marrow Progenitor Cell Subset," *Immunity* 3:459-473 (1995).
Gardner, et al., "T-Lymphopoietic Capacity of Cord Blood-Derived CD34+ Progenitor Cells," *Exp. Hematol.* 26:991-999 (1998).
Gray, et al., "Human Ligands of the Notch Receptor," *Am. J. Pathol.* 154:785-794 (1999).
Jaleco, et al., "Differential Effects of Notch Ligands Delta-1 and Jagged-1 in Human Lymphoid Differentiation," *J. Exp. Med.* 194:991-1001 (2001).

Karanu, et al., "Human Homologues of Delta-1 and Delta-4 Function as Mitogenic Regulators of Primitive Human Hematopoietic Cells," *Blood* 97:1960-1967 (2001).
Kingston, et al., "A Single Stem Cell Can Recolonize an Embryonic Thymus, Producing Phenotypically Distinct T-Cell Populations," *Nature* 317:811-813 (1985).
Krowka, et al., "Human T Cells in the SCID-hu Mouse Are Phenotypically Normal and Functionally Competent," *J. Immunol.* 146:3751-3756 (1991).
Laster, et al., "The Human Thymic Microenvironment: Thymic Epithelium Contains Specific Keratins Associated with Early and Late Stages of Epidermal Keratinocyte Maturation," *Differentiation* 31:67-77 (1986).
McCune, et al., "The SCID-hu Mouse: Murine Model for the Analysis of Human Hematolymphoid Differentiation and Function," *Science* 241:1632-1639 (1988).
Moss, "Redirecting T Cell Specificity by TCR Gene Transfer," *Nature Immunology* 2:900-901 (2001).
Ohishi, et al., "Delta-1 Enhances Marrow and Thymus Repopulating Ability of Human CD34+ CD38 Cord Blood Cells," *J. Clin. Invest.* 110:1165-1174 (2002).
Plum, et al., "Human CD34+ Fetal Liver Stem Cells Differentiate to T Cells in a Mouse Thymic Microenvironment," *Blood* 84:1587-1593 (1994).
Poznansky, et al., "Efficient Generation of Human T Cells from a Tissue-Engineered Thymic Organoid," *Nature Biotechnology* 18:729-734 (2000).
Poznansky, et al., "Inhibition of Human Immunodeficiency Virus Replication and Growth Advantage of CD4+ T Cells and Monocytes Derived from CD34+ Cells Transduced with an Intracellular Antibody Directed against Human Immunodeficiency Virus type 1 Tat," *Human Gene Therapy* 10:2505-2514 (1999).
Rosenzweig, et al., "In Vitro T Lymphopoiesis of Human and Rhesus CD34+ Progenitor Cells," *Blood* 87:4040-4048 (1996).
Rosenzweig, et al., "In Vitro T Lymphopoiesis: A Model System for Stem Cell Gene Therapy for AIDS," *J. Med. Primatol.* 25:192-200 (1996).
Sanchez, et al., "Thymus-Independent T-Cell Differentiation in vitro," *Brit. J. Haematol.* 103:1198-1205 (1998).
Tagoh, et al., "Induction of Recombination Activating Gene Expression in a Human Lymphoid Progenitor Cell Line: Requirement of Two Separate Signals from Stromal Cells and Cytokines," *Blood* 88:4463-4473 (1996).

(Continued)

*Primary Examiner*—Leon B. Lankford, Jr.
*Assistant Examiner*—Allison M. Ford
(74) *Attorney, Agent, or Firm*—Michael A. Sanzo; Law Office of Michael A. Sanzo, LLC

(57) ABSTRACT

The present invention is directed to an in vitro method for producing T lymphocytes. The method involves culturing bone marrow cells on a matrix seeded with keratinocytes and fibroblasts.

26 Claims, No Drawings

OTHER PUBLICATIONS van Ewijk, et al., Thymic Microenvironments, 3-D Versus 2-D?, *Semin. Immunol. 11*:57-64 (1999).

Weijer, et al., Intrathymic and Extrathymic Development of Human Plasmacytoid Dendritic Cell Precursors in vivo, *Blood 99*:2752-2759 (2002).

Yeoman, et al., "Development of CD4 and CD8 Single Positive T Cells in Human Thymus Organ Culture: IL-7 Promotes Human T Cell Production by Supporting Immature T Cells," *Dev. Comp. Immunol. 20*:241-263 (1996).

Zhao, et al., "Highly Disparate Xenogeneic Skin Graft Tolerance Induction by Fetal Pig Thymus in Thymectomized Mice," *Transplantation 72*:1608-1615 (2001).

PROCESS FOR PRODUCING T LYMPHOCYTES

CROSS REFERENCE TO RELATED APPLICATION

The present application claims the benefit of U.S. provisional application No. 60/528,796, filed on Dec. 12, 2003.

STATEMENT OF GOVERNMENT FUNDING

The United States Government has a paid-up license in this invention and the right in limited circumstances to require the patent owner to license others under reasonable terms as provided for by the terms of NIH Grant Nos. T32 AR07098 and RO1 AI25082, awarded by the Department of Health and Human Services.

FIELD OF THE INVENTION

The present invention is directed to an in vitro method for producing T lymphocytes that can be administered to patients for the treatment of a variety of diseases and conditions. The method involves growing bone marrow cells on a three-dimensional matrix under conditions promoting lymphocyte growth.

BACKGROUND OF THE INVENTION

T cells play a central role in the human immune system, mediating the ability to discriminate foreign from self, directing less specific elements of the immune system and serving as a repository for immunologic memory (Heitger, et al., *Blood* 90:850-857 (1997)). The ability to produce T cells in vitro suitable for use in human patients would represent a significant advance in the treatment of immunodeficiencies, infections and malignancies. However, the unique requirements for T cell development have been difficult to replicate in vitro.

T cell differentiation involves an obligate period of development and education in the thymus, an organ that undergoes involution in late adolescence and maintains only a low level of activity in normal adults (Simpson, et al., *Clin. Exp. Immunol.* 19:2610265 (1975); von Gaudecker, *Cell Tissue Res.* 186:507-525 (1978)). Culture systems that mimic the thymus microenvironment and allow the production of T cells from bone marrow precursor cells have generally used animal or unrelated human tissues and this makes these systems unsuitable for the production of T cells for use in humans (Galy, et al., *Immunity* 3:459-473 (1975); Kingston, et al., *Nature* 317: 811-813 (1985); Weijer, et al., *Blood* 99:2752-2759 (2002); McCune, et al., *Science* 241:1632-1639 (1988); Poznansky, et al., *Nat. Biotechnol.* 18:729-734 (2000); Gardner, et al., *Exp. Hematol.* 26:991-999 (1998); Rosenzweig, et al., *Blood* 87:4040-4048 (1996); Tagoh, et al., *Blood* 88:4463-4473 (1996); Yeoman, et al., *Dev. Comp. Immunol.* 20:241-263 (1996); Plum, et al., *Blood* 84:1587-1593 (1994); Krowka, et al., *J. Immunol.* 146:3751-3756 (1991); Freedman, et al., *Nat. Med.* 2:46-51 (1996); Rosenzweig, et al., *J. Med. Primatol.* 25:192-200 (1996)).

The features of the thymus that endow it with the unique capacity to generate T cells have been extensively studied. Epithelial cells, stromal cells, dendritic cells and lymphopoetic cytokines all appear to be required for the differentiation of bone marrow hematopoetic progenitor cells (bmHPC) into mature, functional T cells (Anderson, et al., *Nat. Rev. Immunol.* 1:31-40 (2001)). The three-dimensional architecture of the thymus is also critical to the process of T cell development (van Ewijk, et al., *Semin. Immunol.* 11:57-64 (1999)).

Although unique in their ability to support lymphocyte development, the resident cellular elements of the thymus bear striking similarities to the cells of the skin. Thymic epithelial cells express many of the same keratins as epidermal keratinocytes (Laster, et al., *Differentiation* 31:67-77 (1986)). Hassal's corpuscles, a product of medullar thymic epithelial cells, contain keratins identical to those found in the stratum corneum of skin. In fact, it could reasonably be argued that the major difference between the thymus and skin lies in their distinct three-dimensional architecture.

SUMMARY OF THE INVENTION

The present invention is based upon the development of methods for making T lymphocytes in vitro. The cells produced may be administered to a patient to help alleviate conditions characterized by T lymphocyte loss. In these cases, the bone marrow cells and skin cells used to produce the lymphocytes are derived from the patient. As a result, the T cells produced will not be rejected upon administration. The method may also be used for organ transplant patients, in which case, skin samples will be derived from the individual donating the organ.

Thus, in its first aspect, the invention is directed to a method for producing T lymphocytes in vitro for administration to a patient. The method involves first removing a skin sample from the patient (or from the donor in cases where the T lymphocytes produced in vitro will be administered to an organ transplant patient). Keratinocytes and fibroblasts are then obtained from the skin sample and separately cultured. These cells are then used to colonize a three-dimensional support matrix such as that sold by Cytomatrix. Ideally, colonization of the matrix should take place with a cell preparation containing 30-50% keratinocytes (preferably 35-45%) and 50-70% fibroblasts (preferably 55-65%). After colonization, cells are preferably allowed to remain on the matrix for a period of about 2-10 days, and more preferably 4-8 days. After this time, bone marrow cells derived from the patient are allowed to colonize the matrix. The bone marrow cells are then allowed to grow in a medium containing interleukin-15 (IL-15), interleukin-7 (IL-7) or fms-like tyrosine kinase-3 (Flt-3). Preferably, the interleukins are present at a concentration of 1-100 ng/ml and, more preferably at 4-50 ng/ml. Flt-3 should be present at 10-1,000 ng/ml and preferably at 40-500 ng/ml. The growth of the bone marrow cells is allowed to continue for approximately 3 to 4 weeks. The T lymphocytes are then harvested from the matrix.

Several improvements resulting in preferred embodiments may be incorporated into the procedure and used either separately or, preferably, in combination with one another. In one preferred embodiment, improved yields of T lymphocytes are obtained by irradiating fibroblasts either prior to the time that they are added to the matrix or after they are added to the matrix but before the addition of bone marrow cells. In general, irradiation should involve exposing cells to between 500 and 6,000 rads and preferably to between 2,000 and 4,000 rads.

In another preferred embodiment, improved yield is obtained by incorporating a Notch ligand into preparations during bone marrow growth. Preferably, the Notch ligand is human Delta-1 and is present at a concentration of 3-300 μg/ml and preferably at 10-50 μg/ml. The production of Delta-1 in fibroblasts may be increased by incorporating the coding sequence for human delta-1 into an expression vector and using this to transfect the fibroblasts. The fibroblasts can then be incorporated into the thymus constructs to increase T cell production.

In another preferred embodiment, IL-7, IL-15 and Flt-3 are all present in the method with the interleukins being present at 1-100 ng/ml (and preferably 5-40 ng/ml) and Flt-3 ligand being present at 10-1,000 ng/ml. It is also preferred that bone marrow cells be grown in Iscove's modified Dulbecco's medium supplemented with 5-15% heat-inactivated fetal calf serum (HI-FCS) 1-100 ng/ml of IL-7, 1-100 ng/ml of IL-15 and 10-1,000 ng/ml of Flt-3.

The invention includes the T lymphocytes that are produced by any of the methods described above. It also includes therapeutic methods in which T lymphocytes made by such methods are administered to a patient, preferably a patient suffering from an infectious disease such as HIV infection, or who has experienced a loss of endogenous T lymphocytes due to chemotherapy, immunosuppressive medications or bone marrow transplantation. The procedure may also be used to treat patients undergoing organ transplantation, in which case, the skin cells from which fibroblasts and keratinocytes are derived should be obtained from the organ donor. T cells grown in vitro can then be added back to the organ recipient to reduce the likelihood of rejection.

DETAILED DESCRIPTION OF THE INVENTION

The present invention is directed to a method in which bone marrow cells are removed from an individual and then used in the production of T lymphocytes that can be administered to a patient. The method involves removing a small patch of skin, such as that obtained at a biopsy and using this to separately culture keratinocytes and fibroblasts. In most cases, the patient that will be administered the T lymphocytes produced will also provide the skin sample. However, in cases where the patient is undergoing organ transplantation, the skin sample should be derived from the organ donor. After the keratinocytes and fibroblasts have been cultured, they are colonized on a support matrix. CellFoam™, a porous metal-coated carbon matrix (Cytomatrix, Woburn, Mass.) is suitable for this purpose. However, other porous inert three-dimensional structures should also be suitable. Using 9 mm×9 mm×1.5 mm CellFoam grids, the addition of about $1 \times 10^5$ keratinocytes and $5 \times 10^4$ fibroblasts gives suitable results.

The ratio of fibroblast to keratinocyte is important and, in general, the cells used to colonize the matrix should be comprised of 50-70% fibroblasts and 30-50% keratinocytes. After incubating the preparation at about 37° C. for several days (preferably 2-10 days) bone marrow precursor cells should be added (e.g., 10,000 AC133-positive precursor cells). The entire preparation is then incubated in Iscove's modified Dulbecco's medium supplemented with 10% heat inactivated fetal calf serum (HI FCS), 20 ng/ml of IL-7, 20 ng/ml Il-15 and 100 ng/ml Flt-3 ligand (R&D Systems) and PCN/strep. The cytokines and Flt-3 ligand may be purchased commercially. After allowing T cells to develop and grow, they are harvested and may be administered to a patient.

Improved results can be obtained by adding a Notch ligand to preparations, with the most preferred ligand being Delta-1. Improved results can also be obtained by irradiating cell preparations to reduce the rate at which undesirable cells grow. In general, preparations should be exposed to 500-6,000 rads and preferably 500-6,000 rads.

EXAMPLES

The present example describes specific procedures that can be used for producing T lymphocytes in vitro.

I. Materials and Methods

Isolation and Culture of Keratinocytes and Fibroblasts

Normal human skin was obtained from patients undergoing cosmetic procedures or excision of skin cancers and was divided into 6 mm×6 mm portions. Keratinocytes were isolated by incubation of skin fragments in 2.4 U/ml dispase II (Roche, Indianapolis, Ill.) for 1 hour at 37° C., subsequent removal of the epidermal sheet with tweezers, followed by incubation for 5 minutes at 37° C. in PBS containing 0.25% trypsin and 0.1% EDTA. Keratinocytes were grown in Keratinocyte-SFM (Gibco, Carlsbad, Calif.) supplemented with 25 µg/ml bovine pituitary extract (Gibco), 0.2 ng/ml EGF (Gibco), 0.3 mM $CaCl_2$, 100 IU/ml penicillin and 100 µg/ml streptomycin (PCN/Strep). Fibroblasts were isolated by mincing of dermal skin fragments and incubation in HBSS with 2.5 mg/ml trypsin and 5 mg/ml collagenase for one hour. Fibroblasts were cultured in DMEM/F12 (Gibco) supplemented with 15% FCS (Sigma, St. Louis, Mo.), 10 ng/ml EGF, and PCN/Strep. Keratinocytes and fibroblasts were passaged fewer than five times before use in experiments.

Thymus Construct 9 mm×9 mm×1.5 mm Cellfoam grids (Cytomatrix, Woburn, Mass.) were incubated in a solution of 100 µg/ml rat tail collagen I (BD Biosciences, Bedford, Mass.) in PBS for 30 minutes at 37° C. and rinsed twice in PBS. $1 \times 10^5$ keratinocytes and $5 \times 10^4$ fibroblasts were added to each grid and incubated for 4 hours at 37° C., 5% $CO_2$. Nonadherent cells were removed by transferring the grids to new 24 well plates. 2 ml of culture medium was added to each grid and consisted of a 1:1 mix of the fibroblast and keratinocyte media described above. The constructs were then cultured for six days and the medium was changed every other day. Irradiated grids were treated with 3000 Rads on day six. For γ-interferon treated grids, 50 ng/ml γ-interferon (R&D Systems, Minneapolis, Minn.) was included in the culture medium from plating until day six. On day seven, 10,000 normal human bone marrow $AC133^+$ precursor cells (AllCells, LLC, Berkeley, Calif.) were added to each grid and the unit was cultured in Iscove's modified medium (Mediatech, Herndon, Va.) with 10% HI FCS (Sigma), 20 ng/ml IL-7, 20 ng/ml IL-15, and 100 ng/ml Flt-3 ligand (R&D Systems) and PCN/Strep. One half of the medium was aspirated and replaced three times weekly and the culture was maintained for three to four weeks.

Immunofluorescence Microscopy and Flow Cytometry Analysis

Immunofluorescence microscopy of thymus constructs was performed by rinsing the constructs in PBS, followed by fixation in 100% acetone for 5 minutes and rehydration in PBS. Grids were then incubated with 1:50 dilution of mixed monoclonal mouse anti-pan cytokeratin ascites (Sigma) and 1:20 dilution of goat anti-vimentin antiserum (Sigma) in PBS/1% BSA for 45 minutes at room temperature. Grids were rinsed twice and incubated in secondary antibodies FITC-rabbit anti-goat IgG (Zymed, San Francisco, Calif.) and Rhodamine Red-X-conjugated rabbit anti-mouse IgG (Jackson ImmunoResearch Labs, West Grove, Pa.) for 30 minutes at room temperature. Grids were then mounted on microscope slides using Prolong Antifade Kit (Molecular Probes, Eugene, Oreg.) and examined by fluorescence microscopy. Flow cytometry analysis of T cells was performed using directly conjugated monoclonal antibodies (BD Biosciences, San Diego, Calif.). Analysis of flow cytometry samples was performed on a Becton Dickinson FACScan instrument.

TREC Analysis

DNA was isolated from $1 \times 10^5$ cells as per protocol (QIAamp DNA blood mini kit, Qiagen, Valencia, Calif.). 0.5 μg of DNA was used in each GAPDH or TREC PCR reaction as previously described (Douek, et al., *Nature* 396:690-5 (1998)).

Immobilization of Delta$^{ext\text{-}IgG}$ 24 well tissue culture plates were coated with 30 μg/ml mouse anti-human IgG (Pharmingen, San Diego, Calif.) in 0.1 M NaHCO$_3$, pH 9.6 for two hours at 37° C. Wells were rinsed twice with PBS after which 10 μg/ml of Delta$^{ext\text{-}IgG}$ in PBS with 2% FCS was added. The plates were incubated overnight at 4° C. The solution was then aspirated and the thymus constructs were placed into these wells before seeding with bmHPC.

T Cell Receptor Spectratype Analysis

TCR-CDR3 length analysis was performed as previously described (Pilch, et al., *Clin. Diagn. Lab. Immunol.* 9:257-266 (2002)). Briefly, total RNA was isolated from $8 \times 10^5$ cells and reverse transcribed into cDNA (SV total RNA isolation system, Promega, Madison, Wis.). PCR reactions were performed using primers specific for the TCR alpha chain and individual primers for the 26 TCR beta chains. Additional run-off reactions were performed using fluorophore labelled primers and labelled products were analyzed using a DNA sequencer and Genescan software.

T Cell Functional Assays

To assess mitogen induced proliferation, cells produced in the thymus construct were incubated in RPMI/10% FCS for 72 hours with and without 5 μg/ml of PHA (Sigma). 1 mM BrdU was included in the culture medium for the last 18 hours of treatment. Cells were collected, stained for surface expression of CD3 using directly conjugated anti-CD3 (BD Biosciences), then fixed in 0.5% paraformaldehyde, permeabilized, stained for intracellular BrdU as per protocol (BrdU Flow Kit, BD Biosciences) and examined by flow cytometry. Scatter plots were generated by gating on CD3$^+$ cells. To examine surface CD69 expression, T cells were incubated in RPMI/10% FCS with and without 5 μg/ml concanavalin A (Calbiochem, La Jolla, Calif.) for four hours. Cells were then collected, stained for CD69 expression using directly conjugated CD69 mAb (BD Biosciences) and assayed by flow cytometry with gating on CD3$^+$ cells. Production of TNF-α was assayed after treatment of cells with RPMI/10% FCS with or without 5 μg/ml concanavalin A for 6 hours. 10 μg/ml Brefeldin A (Calbiochem) was included in the culture medium for the last 5 hours of incubation. Cells were then stained for surface marker expression, fixed, permeabilized, stained with PE-conjugated anti-TNFα antibody (BD Biosciences) and examined by flow cytometry.

II. Results

Composition and Characterization of the Thymus Construct

A number of different approaches were taken to replicate the thymus microenvironment using cells derived from human skin. The goal of the process was to produce a construct that contained large numbers of healthy epithelial cells intermingled with stromal cells. Fibroblasts, keratinocytes and lymphocytes each have distinct growth requirements in vitro, and typically require very different media for their propagation. A significant amount of preliminary work was therefore required to design a system that could accommodate all three types of cells in a healthy, growing state.

Ultimately, we chose a system that gave the most reproducible and promising results. This procedure involved expanding keratinocytes and fibroblasts as separate populations in vitro from samples of discarded human skin. These cells were then seeded together onto Cellfoam cell growth matrices. Cellfoam is three-dimensional tantalum-coated carbon matrix originally designed as an artificial bone matrix and used in previous xenogenic in vitro thymus cultures (Cytomatrix, Woburn, Mass.) (Poznansky, et al., *Nat. Biotechnol.* 18:729-34 (2000)). The constructs were cultured for six days, after which, human bone marrow derived AC133$^+$ hematopoetic precursor cells were injected into the colonized grid, and the combined cultures were maintained in culture for three to four weeks in the presence of the pro-lymphopoetic cytokines IL-7, IL-15 and Flt-3 ligand.

Immunofluorescence microscopy of productive thymus constructs demonstrated the presence of viable populations of both keratinocytes and fibroblasts on the three-dimensional matrix even after three weeks of culture in Iscove's medium, a medium well suited to T cell development but not normally supportive of fibroblast and keratinocyte growth. Dendritic cells, distinguished by their high expression of MHC Class II and lack of CD14, were demonstrable by immunofluorescence microscopy only if bone marrow hematopoetic precursor cells (bmHPC) were added to the construct, indicating that these cells are of bone marrow origin.

Characterization of T Cells Produced in the Thymus Construct

We first analyzed the cells produced by the construct using flow cytometry. Mixed two-dimensional cultures of fibroblasts and keratinocytes did not support T cell development from bmHPC. Similarly, three-dimensional constructs containing only fibroblasts or keratinocytes and seeded with bmHPC did not produce T cells. In contrast, matrices containing both keratinocytes and fibroblasts supported the development of cells that expressed T lymphocyte cell surface markers, including the CD3/TCR complex. Optimal T cell production was observed when matrices contained at least 40-50% epithelial cells. Single $9 \times 9 \times 1.5$ mm constructs produced in the range of $6 \times 10^5$ CD3$^+$ T cells, comprising approximately 10% of the total cell output. In addition to T cells, we observed production of CD14$^-$HLA-DR$^{hi}$ dendritic cells (approximately 20-40%) and CD14$^+$ myeloid cells, and a variable number of CD56$^+$ cells.

During development in the thymus construct, progenitor cells initially expressed CD34 but lost expression of this marker as increasing levels of CD3 were acquired. This loss of CD34 and gain of CD3 is seen during normal T cell development in the thymus (Anderson, et al., *Semin Immunol* 12:457-64 (2000)). Progenitor cells in our system were initially negative for both CD4 and CD8. Transient production of double-positive CD4$^+$CD8$^+$ T cells was noted between days 7 to 10 of culture. By day 21, single-positive CD4$^+$ and CD8$^+$ cells were present. Normally developing thymocytes also progress from double-negative CD4$^-$CD8$^-$ cells to double-positive CD4$^+$CD8$^+$ cells and subsequently on to mature single-positive CD4$^+$ or CD8$^+$ cells. Double-positive CD4$^+$CD8$^+$ T cells, demonstrably present in our thymus construct, are a cell population normally found exclusively in the thymus. By varying the culture conditions, we were able to influence the production of CD4$^+$ versus CD8$^+$ cells. Pretreatment of the construct with IFNγ prior to the addition of bmHPC led to increased numbers of single positive CD8+ cells and irradiation of the construct prior to precursor addition of bmHPC produced larger numbers of single positive CD4 cells. A more equal distribution of CD4 and CD8 cells was produced in the absence of these treatments.

Skin and other epithelial tissues have been reported to support the development of T cells with a γδ T cell receptor, while αβ T cells seem to be uniquely produced by the thymus (Spits, *Nat. Rev. Immunol.* 2:760-72 (2002)). We next asked whether the T cells that developed in our model expressed γδ TCR. Of the CD3+ cells produced in the construct, more than 95% were αβ TCR T cells and there were few γδ TCR T cells observed. Immature thymocytes undergoing positive selection express CD45RO. Loss of CD45RO and gain of CD45RA expression occurs in mature naïve T cells prior to their release from the thymus. A significant proportion of T cells produced in the thymus construct expressed CD45RA, suggesting that these cells are naïve T lymphocytes. A continuum of expression of CD45RA and RO was seen, consistent with a dynamic process of up and down regulation.

Newly Produced T Cells Contain TCR Excision Circles

To ensure that the T cells produced in our system are naive, newly produced T cells and not simply expanded populations of contaminating mature T cells, we tested output cells from our construct for the presence of T cell receptor excision circles (TREC). Newly produced T cells contain episomal circles of DNA called TREC that are produced as a by-product of the recombination of TCR genes (Douek, et al., *Nature* 396:690-695 (1998)). Mature thymocytes and naive T cells recently released from normal thymus contain TREC, but proliferation of T cells in the periphery dilutes out TREC because these DNA episomes do not replicate during cell division. TREC have therefore been used to identify naive T cells and recent thymic emigrants. We performed qualitative PCR analysis on both input bmHPC and lymphocytes produced in the construct. The results indicated an absence of TREC in the input cell population (bmHPC), and the presence of TREC in lymphocytes produced in the construct. These findings indicate that cells derived from bmHPC underwent rearrangement of the T cell receptor genes within the skin derived thymus construct.

T Cell Production is Enhanced in the Presence of the Notch Ligand Delta-1

The Notch ligand Delta-1 has been shown to enhance T cell development via maintenance and expansion of progenitor cells, induction of lymphoid differentiation at the expense of myeloid differentiation, and the biasing of lymphocyte production towards T and away from B cells (Jaleco, et al., *J. Exp. Med.* 194:991-1002 (2001); Ohishi, et al., *J. Clin. Invest.* 110:1165-1174 (2002); Karanu, et al., *Blood* 97:1960-1967 (2001)). To determine if inclusion of Delta-1 in our culture system could increase lymphocyte production, a construct containing the extracellular domain of human Delta-1 fused to the Fc portion of human IgG1 (Delta$^{ext-IgG}$) was immobilized on culture wells containing the thymus constructs. Inclusion of the Delta$^{ext-IgG}$ overall T cell production from 15% to 33% in a representative experiment while maintaining robust production of both CD4+ and CD8+ T cells.

In other experiments the coding sequence for the notch ligand human delta-1 (see Gray, et al., *Am. J. Pathol.* 154(3): 785-794 (1999)) was inserted into a lentiviral expression cassette (Virapower lentiviral expression system utilizing a pLenti6/V5-DEST vector, Invitrogen) and used to generate infectious lentivirus. Passage 1 human fibroblasts were transduced with the lentivirus and antibiotic selection was used to select for fibroblasts stably expressing high levels of the delta-1 protein. These fibroblasts were then incorporated into the thymus constructs with resultant increased level of T cell production.

Newly Produced T Cells Express a Diverse T Cell Receptor Repertoire

To examine the T cell receptor diversity of cells produced in the thymus construct, 8×10$^5$ newly produced T cells were subjected to spectratyping via TCR-CDR3 length analysis. This technique allows identification of both Vβ usage as well as diversity within each Vβ family. Results demonstrate that T cells of all 26 Vβ subfamilies tested were represented in the small population of newly produced T cells subjected to analysis. There was also significant diversity in 22 of 26 Vβ families. More limited diversity was observed in only 4 of the Vβ families (Vβ8, 19, 23 and 24). Thus, the thymus construct generated a complex T cell repertoire with no readily apparent Vβ bias.

Newly Produced T Cells are Mature and Functional

Mature and functional T cells are distinguished by their ability to proliferate, express the activation antigen CD69, and produce cytokines in response to stimulation through the TCR CD3 complex. To determine whether the T cells produced in our system are mature and functional, we evaluated the response of these cells to T cell mitogens. T cells produced in the thymus construct proliferated in response to treatment with phytohemagglutinin. Newly produced CD4+ and CD8+ single positive T cells stimulated with concanavalin A expressed robust levels of the early activation marker CD69. A subset of these activated cells also produced TNF-α as demonstrated by intracellular flow cytometry.

III. Discussion

The present example describes an in vitro culture system for the production of human T cells. The presence of both keratinocytes and fibroblasts in a complex three-dimensional arrangement is essential for T cell production, and T cell yield is augmented by the presence of IL-7, IL-15, and Flt-3 ligand. The lack of CD3+ cells in the input cell population, the production of double-positive CD4+CD8+ intermediate cells, and the expression of CD45RA and TREC on CD3+ lymphocytes from the construct support the view that the T cells observed in the system are in fact naïve, newly produced T cells. T cells produced by the construct exhibit a diverse T cell repertoire, additional evidence that these cells are not derived from proliferation of a few contaminating mature T cells. T cell development is a complex, multistage process.

During the process of positive selection, developing T cells die after completion of TCRα rearrangements unless they are rescued by a low-affinity interaction of the TCR complex with MHC antigens expressed on thymic epithelial cells. Successful completion of positive selection is an absolute requirement for the production of single positive CD4+ and CD8+ cells. The production of single positive, mature T cells in our thymus construct system is therefore presumptive evidence that keratinocyte-derived epithelial cells are capable of supporting positive selection of human lymphocyte precursor cells.

Our results also demonstrate increased production of T cells in the presence of the Notch ligand Delta-1. The Notch family of molecules are highly conserved transmembrane receptors that regulate cell fate decisions and differentiation in many developmental systems (Artavanis-Tsakonas, et al., *Science* 268:225-32 (1995)). Activation of Notch signaling is stimulated by binding of Notch ligands, a family that includes Jagged-1, Jagged-2, and Delta-1, -2, -3, and -4 which are themselves transmembrane proteins. Notch-1 and Notch-2 are expressed by CD34+ bone marrow hematopoetic precursor cells (Milner, et al., *Blood* 83:2057-2062 (1994)) and Notch ligands are expressed in the thymus, as well as bone marrow stromal cells and fetal liver (Stier, et al., *Blood*

99:2369-2378 (2002)). The Notch ligand Delta-1 enhances T cell development via maintenance and expansion of progenitor cells, induction of lymphoid differentiation over myeloid differentiation, and the biasing of lymphocyte production towards T and away from B cells.

Notch signalling also plays a role in epidermal development, leading to keratinocyte growth arrest and differentiation (Rangarajan, et al., *EMBO J.* 20:3427-3436 (2001)). Notch receptors are expressed throughout the epidermis, while Notch ligands are expressed in a more compartmentalized fashion. Delta-1 is expressed on epithelial stem cells and may protect stem cells from Notch-mediated differentiation while inducing differentiation in neighbouring cells (Lowell, et al., *Current Biology* 10:491-500 (2000)). Inclusion of immobilized Delta$^{ext-IgG}$ in the tissue culture wells containing the thymus constructs led to increases in T cell production. While this effect was significant, we would expect an enhanced effect of Delta-1 were it immobilized directly on the stromal cells of the thymus construct.

Two studies have reported T cell development using tissues not derived directly from the thymus. A stromal cell line derived from mouse bone marrow supported human T cell development (Tagoh, et al., *Blood* 88:4463-4473 (1996)) and mononuclear cells from human cord blood were also shown to be capable of supporting T cell differentiation (Sanchez, et al., *Br. J. Haematol* 103:1198-205 (1998)). In the first study, the use of animal tissues precludes the use of this system in humans. The second system is attractive in that it uses only human tissues but it does not allow for the ability to use only tissues derived from a single individual adult. Positive selection requires interaction of thymocytes with the epithelial cells of the thymus while negative selection is dependent on bone marrow derived dendritic cells resident in the thymus. Optimally, a microenvironment used to support the development of T cells for use in a human patient would utilize only autologous tissues from that individual. The unique feature of the present system is its ability to generate new T cells using only skin and bone marrow, tissues that can be readily obtained from an adult individual.

The clinical applications for newly produced, patient-specific T cells are quite broad. Naïve autologous T cells could be produced for the treatment of patients who have lost peripheral T cells secondary to HIV infection or to therapeutic interventions such as cancer chemotherapy, immunosuppressive medications, or recent bone marrow transplantation. These patients are currently susceptible to infection and some opportunistic malignancies, often with devastating consequences (Boshoff, et al., *Nat. Rev. Cancer* 2:373-82 (2002)). In addition, T cells specific for particular infections or malignancies could be produced by transduction of bmHPC with TCR genes or constructs specific for infection or tumor-associated antigens (Moss, P., *Nat. Immunol.* 2:900-901 (2001); Poznansky, et al., *Hum. Gene Ther.* 10:2505-14 (1999)). Lastly, cross-species organ transplant experiments have shown that donor-specific tolerance to transplanted tissues can be induced by the implantation of donor thymus tissue into the graft recipient (Zhao, et al., *Transplantation* 72:1608-1615 (2001)). Assuming that similar mechanisms are active in humans, an implanted thymus construct derived from donor skin could be used to induce donor-specific tolerance prior to allogeneic organ transplantation. The induction of tolerance to organ transplants could significantly reduce the morbidity and mortality of transplant patients by decreasing the need for immunosuppressive medications.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method for producing T lymphocytes in vitro for administration to a patient, comprising:
    (a) removing a skin sample from said patient;
    (b) separately culturing keratinocytes and fibroblasts derived from said skin sample;
    (c) colonizing a support matrix with the cultured keratinocytes and fibroblasts of step (b);
    (d) obtaining hematopoietic precursor cells from the bone marrow of said patient;
    (e) adding said bone marrow hematopoietic precursor cells to the colonized matrix of step (c);
    (f) culturing said bone marrow hematopoietic precursor cells on said support matrix in the presence of one or more factors selected from the group consisting of IL-15; IL-7; and Flt-3 ligand, so as to induce production of T lymphocytes; and
    (g) harvesting T lymphocytes from said matrix.

2. The method of claim 1, wherein in step (c), said support matrix is colonized with 30-50% keratinocytes and 50-70% fibroblasts and then maintained at a temperature of 34-40° C. for a period of 2-10 days.

3. The method of claim 2, wherein said support matrix is colonized with 35-45% keratinocytes and 55-65% fibroblasts.

4. The method of claim 1, further comprising an irradiation step in which said fibroblasts are irradiated either prior to addition to said matrix in step (c) or after the colonization of step (c) but prior to the addition of said bone marrow precursor cells.

5. The method of claim 4, wherein said irradiation comprises treatment with 500-6,000 rads.

6. The method of claim 5, wherein said irradiation comprises treatment with 2,000-4,000 rads.

7. The method of claim 1, wherein step (f) comprises culturing said bone marrow precursor cells on said support matrix in the presence of IL-15, IL-7 and Flt-3 ligand.

8. The method of claim 1, wherein the culturing of step (f) is further carried out in the presence of the Notch ligand Delta-1.

9. The method of claim 8, wherein said Notch ligand is added to a concentration of 3-300 µg/ml.

10. The method of claim 9, wherein said Notch ligand is added to a concentration of 10-50 µg/ml.

11. The method of claim 1, wherein said IL-7 and IL-15 are present at a concentration of 1-100 ng/ml and Flt-3 ligand is present at 10-1,000 ng/ml.

12. The method of claim 11, wherein IL-7 and IL-15 are present at a concentration of 5-40 ng/ml and Flt-3 is present at a concentration of 40-500 ng/ml.

13. The method of claim 1, wherein the culturing of step (f) comprises culturing said bone marrow precursor cells in Iscove's modified Dulbecco's medium supplemented with 5-15% heat inactivated fetal calf serum (HI FCS), 1-100 ng/ml of IL-7 and IL-15 and 10-1,000 ng/ml of Flt-3 ligand.

14. A method for producing T lymphocytes in vitro for administration to a patient who has undergone transplantation of an organ donated by a donor, said method comprising:
    (a) removing a skin sample from said donor;
    (b) separately culturing keratinocytes and fibroblasts derived from said skin sample;
    (c) colonizing a support matrix with the cultured keratinocytes and fibroblasts of step (b);

(d) obtaining hematopoietic precursor cells from the bone marrow of said patient;

(e) adding bone marrow hematopoietic precursor cells to the colonized matrix of step (c);

(f) culturing said bone marrow hematopoietic precursor cells on said support matrix in the presence of one or more factors selected from the group consisting of IL-15; IL-7; and Flt-3 ligand, so as to induce production of T lymphocytes; and (g) harvesting T lymphocytes from said matrix.

15. The method of claim 14, wherein in step (c), said support matrix is colonized with 30-50% keratinocytes and 50-70% fibroblasts and then maintained at a temperature of 34-40° C. for a period of 2-10 days.

16. The method of claim 15, wherein said support matrix is colonized with 35-45% keratinocytes and 55-65% fibroblasts.

17. The method of claim 14, further comprising an irradiation step in which said fibroblasts are irradiated either prior to addition to said matrix in step (c) or after the colonization of step (c) but prior to the addition of said bone marrow precursor cells.

18. The method of claim 17, wherein said irradiation comprises treatment with 500-6,000 rads.

19. The method of claim 17, wherein said irradiation comprises treatment with 2,000-4,000 rads.

20. The method of claim 18, wherein step (f) comprises culturing said bone marrow precursor cells on said support matrix in the presence of IL-15, IL-7 and Flt-3 ligand.

21. The method of claim 14, wherein the culturing step (f) is further carried out in the presence of the Notch ligand Delta-1.

22. The method of claim 21, wherein said Notch ligand is added to a concentration of 3-300 µg/ml.

23. The method of claim 22, wherein said Notch ligand is added to a concentration of 10-50 µg/ml.

24. The method of claim 18, wherein said IL-7 and IL-15 are present at a concentration of 1-100 ng/ml and Flt-3 ligand is present at 10-1,000 ng/ml.

25. The method of claim 24, wherein IL-7 and IL-15 are present at a concentration of 5-40 ng/ml and Flt-3 is present at a concentration of 40-500 ng/ml.

26. The method of claim 14, wherein the culturing of step (f) comprises culturing said bone marrow precursor cells in Iscove's modified Dulbecco's medium supplemented with 5-15% (HI FCS), 1-100 ng/ml of IL-7 and IL-15 and 10-1,000 ng/ml of Flt-3 ligand.

* * * * *